(12) United States Patent
Ganz (10) Patent No.: US 9,131,909 B1
(45) Date of Patent: Sep. 15, 2015

(54) LOW EMISSION FULL MOUTH XRAY APPARATUS

(71) Applicant: Jonathan Ganz, Orangevale, CA (US)

(72) Inventor: Jonathan Ganz, Orangevale, CA (US)

( * ) Notice: Subject to any disclaimer, the term of this patent is extended or adjusted under 35 U.S.C. 154(b) by 60 days.

(21) Appl. No.: 14/242,708

(22) Filed: Apr. 1, 2014

(51) Int. Cl.
*A61B 6/14* (2006.01)

(52) U.S. Cl.
CPC ...................................... *A61B 6/145* (2013.01)

(58) Field of Classification Search
CPC .......... A81B 6/14; A61B 6/145; A61B 6/466; A61B 6/505
USPC ................................................. 378/38–40, 62
See application file for complete search history.

(56) References Cited

U.S. PATENT DOCUMENTS

| 5,113,424 | A | * | 5/1992 | Burdea et al. | .................. 378/170 |
| 6,223,067 | B1 | * | 4/2001 | Vilsmeier et al. | ............. 600/426 |
| 2010/0074401 | A1 | * | 3/2010 | Kayzerman | ..................... 378/38 |

* cited by examiner

Primary Examiner — Courtney Thomas (57) ABSTRACT

The apparatus the present invention provides the ability to take an x-ray image of an entire mouth in one exposure while significantly reducing the amount of escaped x-ray energy. This is accomplished by using a full mouth insert that has slots for two strips of film, one for the upper set of teeth and one for the lower set of teeth, or an embedded imaging sensor.

14 Claims, 6 Drawing Sheets

LOW EMISSION FULL MOUTH XRAY APPARATUS

This application for patent claims the benefit of U.S. provisional application 61/808,453 filed Apr. 4, 2013.

BRIEF DESCRIPTION

The subject of this invention relates to x-ray imaging, specifically, to a full mouth x-ray apparatus. The disclosed invention presents an apparatus that allows the entire mouth to be imaged in one exposure, with very low radiation escape providing superior protection for the patient. The disclosed invention may be used with contemporary medical/dental x-ray devices.

BACKGROUND OF THE INVENTION

The need for the medical/dental practitioners to take x-ray images of the human mouth remains as necessary modernly as it has historiocally. Over time the technology has remained the same, but the equipment used to implement the technology has continued to advance.

Contemporarily, if an x-ray image of patient's full mouth is needed, it is done in segments. That is, a film card or image sensor is placed in one quadrant or another of the patient's mouth, the image is taken and the film card removed or the image reviewed on a computer system. A new film card or image sensor is placed in a different quadrant of the mouth and another image taken. This process is repeated until all areas of the mouth have been imaged.

While functional, this method has several serious drawbacks. First, the patient is exposed to multiple x-ray bursts. While the dosages are low, they nonetheless must be repeated in order to make a complete set of images for analysis. Second, the x-ray transmitter is oriented from the outside in. This means that each burst of x-ray energy passes through the patient's cheek, through the teeth and then on to the inner mouth. From there the x-ray energy continues to pass through to the thyroid, and in general is not recommended for women who are pregnant, even if a lead shield is used. This means that for a full set of images, the inner mouth may see as many as eighteen to thirty-six bursts of x-ray energy. According to the American Dental Association, the dosage of x-ray energy received by a dental patient is around 0.150 mSv for a full mouth series.

A third drawback of contemporary methods is that the operator of the apparatus must exit the room while the x-ray burst is applied. This is done to prevent the operator from being exposed to an objectionable accumulation of x-ray energy. A fourth drawback of current methods is the need for the operator to focus the equipment in the blind. That is, the film is placed in the patient's mouth, the operator manipulates the horn of the transmitter, leaves the room and then shoots the image. On many occasions the horn is misaligned, for example, a child moves prior to the burst of energy, thus the shot has to be repeated in order to garner a usable image.

A more advanced technique uses an imaging sensor in the patient's mouth rather than a film card. The imaging sensor is wired to a computer system that receives the x-ray data from the digital image sensor, processes it and then displays it on a screen. While this method improves the time required to take and analyze x-ray images, it still requires the four separate exposures to the x-rays and has the same excess radiation problem.

While these contemporary methods work well enough, what would be desirable would be an apparatus that allows the full mouth to be imaged in one exposure. Moreover, it would be even more desirable if this could be accomplished by an apparatus that prevented the escape of excess x-ray energy to the interior of the patient's mouth.

SUMMARY OF THE INVENTION

The apparatus the present invention provides the ability to take an x-ray image of an entire mouth in one exposure while significantly reducing the amount of escaped x-ray energy. This is accomplished by using a full mouth insert that has slots for two strips of film, one for the upper set of teeth and one for the lower set of teeth, or an embedded imaging sensor.

The full mouth insert of the present invention resembles the conventional teeth guard used by athletes. It is comprised of two u-shaped cavities, one for the upper set of teeth and one for the lower set of teeth. Several sizes are available in order to cover a wide range of patients, from children to adult.

Both the upper and lower u-shaped cavities have a slot for accepting a film strip of the contemporary type. Once the film strip is loaded into the slots, the full mouth apparatus is placed in the patient's mouth and the exposure taken. In an alternative embodiment, a more advanced apparatus contains an x-ray imaging sensor that covers both the upper and lower cavities that is wired directly to a computer. Once the exposure is complete, the computer analyzes and displays the patient's images for immediate review.

Additionally, the full mouth insert has a waveguide means that directs the beam of x-ray energy from the horn of the transmitter to the inside of the mouth. Advantageously, the waveguide of the present invention is configured such that conventional x-ray machines may be used to accomplish the x-ray process. Misalignment of the x-ray machine is minimized since the waveguide of the present invention interfaces in an accurate and repeatable manner with the horn of the contemporary x-ray machine. Once the x-ray energy is present in the inside of the inner u-shaped segment, it is directed outward, through the teeth and then into a barrier that significantly reduces any excess radiation from exiting the apparatus. In this way the apparatus allows an accurate image of the entire mouth with only one shot with very low possibility of misalignment.

The present invention is discussed in detail below in conjunction with the drawings listed below. As will be evident, the apparatus of the present invention overcomes the disadvantages of the prior art.

DETAILED DESCRIPTION OF PREFERRED EMBODIMENTS

As described briefly above, the apparatus of the present invention may be used with a variety of contemporary x-ray transmitters, including computerized x-ray imaging systems, for example, those found in hospitals and dental offices. See, for example, the ProX series of machines from Planmeca, Inc., Roselle, Ill.

Figure 1:
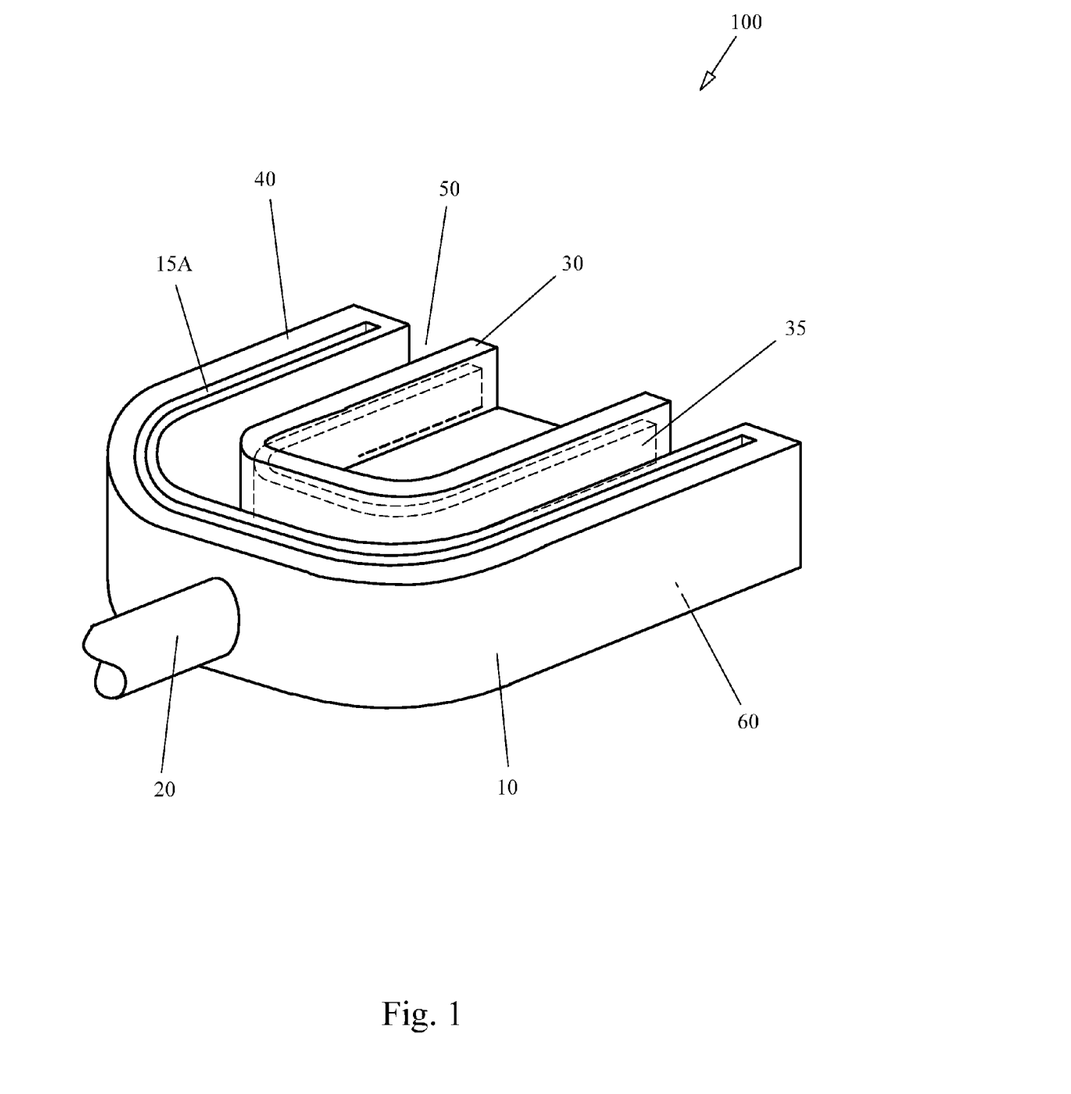
FIG. 1: shows the full mouth insert of a first embodiment of the apparatus of the present invention.

FIG. 1 provides an overview 100 of a first embodiment of the apparatus of the present invention. This first embodiment is for use with contemporary film based x-ray imaging. For example, film such as Kodak E+ film from Eastman Kodak, Rochester, N.Y. A full mouth insert 10 has a pair of cavities 50 and 60 to receive the teeth of a patient to be imaged. The upper tooth cavity 50 accommodates the upper set of teeth while the lower tooth cavity 60 (not shown in detail) accommodates the lower teeth. The full mouth insert 10 can be made in several sizes to allow use on any size mouth, from early childhood to adult.

As described in detail below, the full mouth insert 10 has two u-shaped segments 30 and 40. A first outer u-shaped segment 40 has a set of narrow film slots 15A and 15B that accommodate strips of x-ray film. The upper narrow film slot 15A has a lower narrow film slot counterpart 15B not shown in the figure, but understood to be a mirror replica of the upper narrow film slot 15A. A second inner u-shaped segment 30 is formed around an x-ray waveguide means 35. The x-ray waveguide means 35 occupies the second inner u-shaped segment 30 of the full mouth insert 10. The waveguide means 35 accepts an incoming beam of x-ray radiation bursts from the horn of an x-ray transmitter through focusing tube 20. Focusing tube 20 interfaces with waveguide means 35 in such a way as to pass the x-ray energy to the waveguide means 35 without allowing x-ray energy to escape. Waveguide means 35 then emits the x-ray energy through the patient's teeth to the film contained in the upper and lower narrow film slots 15A and 15B [shown in FIGS. 2 and 3].

Full mouth insert 10 is made from some pliable material, for example plastic, allowing the waveguide means 35 to be encased and the upper and lower narrow film slots 15A and 15B to be formed on a mass produced basis. In this first embodiment the full mouth insert 10 is made from plastic, but as will be recognized by those of skill in the art, other materials, such as hard rubber, could be used without departing from the spirit of the invention, thus the scope of the invention is limited only by the claims. Not shown in FIG. 1 but described in detail below, the full mouth insert 10 also has a set of x-ray impeding barriers which prevent x-ray energy from escaping the apparatus either to the outside of the patient's mouth or to the inside of the patient's mouth.

Figure 2:
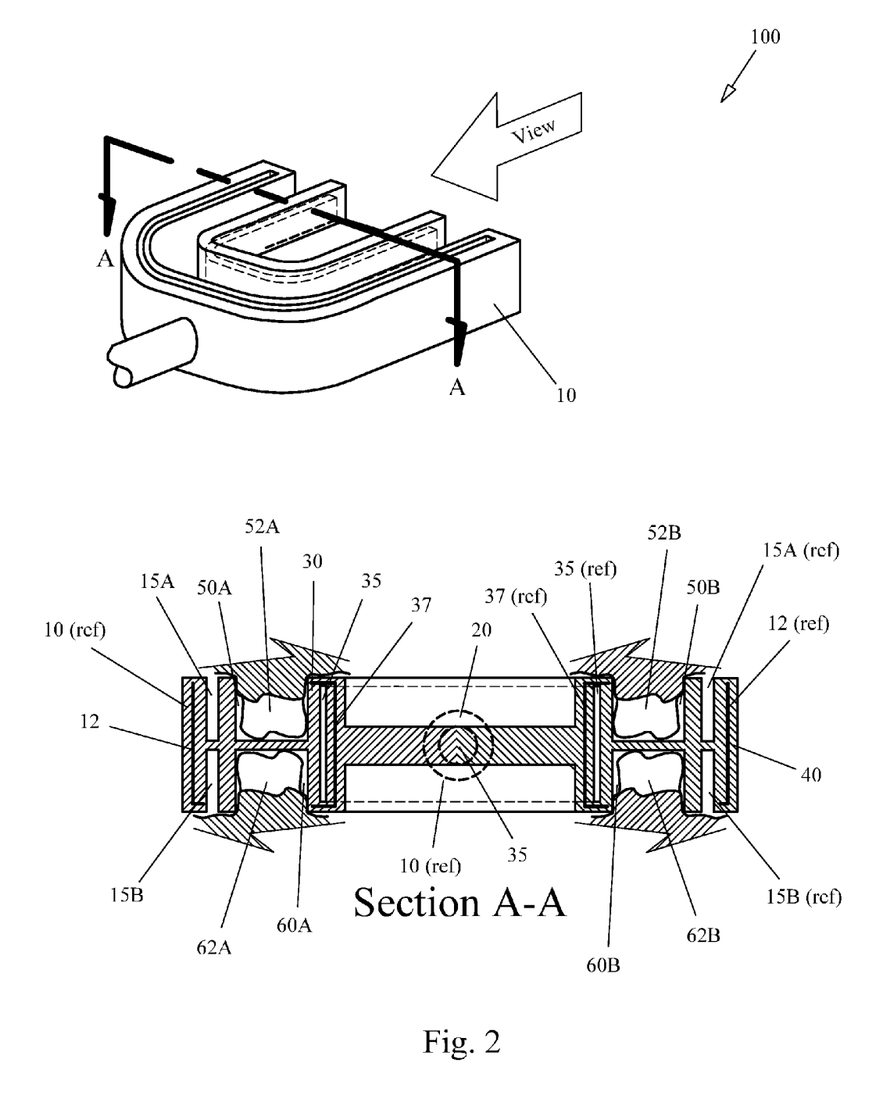
FIG. 2: is a latitudinal cross section of a first embodiment of the full mouth insert of the present invention.

Looking now at FIG. 2, the apparatus of the present invention 100 shows the full mouth insert 10 in latitudinal cross section A-A. Note that the viewing perspective is from the rear of the full mouth insert 10 towards the front. This view is taken to provide the clearest detail of the plurality of features internal to the full mouth insert 10.

Four tooth cavities, two upper tooth cavities 50A and 50B, and two lower tooth cavities 60A and 60B are shown. A patient's teeth 52A, 52B, 62A and 62B are shown to provide a reference for the reader. Focusing tube 20 interfaces with waveguide means 35. Waveguide means 35 occupies the interior of the inner u-shaped segment 30 of the full mouth insert 10. As can be seen, an x-ray energy impeding barrier 37 lies to the inside of the inner u-shaped segment 30 of the full mouth insert 10. The x-ray energy impeding barrier 37 prevents x-ray energy from escaping to the inside of the patient's mouth.

An outer u-shaped segment 40 contains the narrow film slots 15A and 15B. Strips of x-ray film are placed in these slots, reacting to the x-ray energy passing through the teeth 52A, 52B, 62A and 62B of the patient being x-rayed, striking the film and creating an image. Lying to the outside of the narrow film slots 15A and 15B is an x-ray energy impeding barrier 12 that performs the same function as the x-ray energy impeding barrier 37 discussed just above. The function of x-ray energy impeding barrier 12 is to prevent x-ray energy from escaping to the outside through the patient's cheek. In this way x-ray energy is sent to the waveguide means 35, through the teeth of the patient being x-rayed, and onto the film for imaging. The combination of the x-ray impeding barriers 12 and 37 prevent the majority of the x-ray energy from escaping the boundaries of the apparatus thereby minimizing exposure to the patient and to the outside environment.

Figure 3:
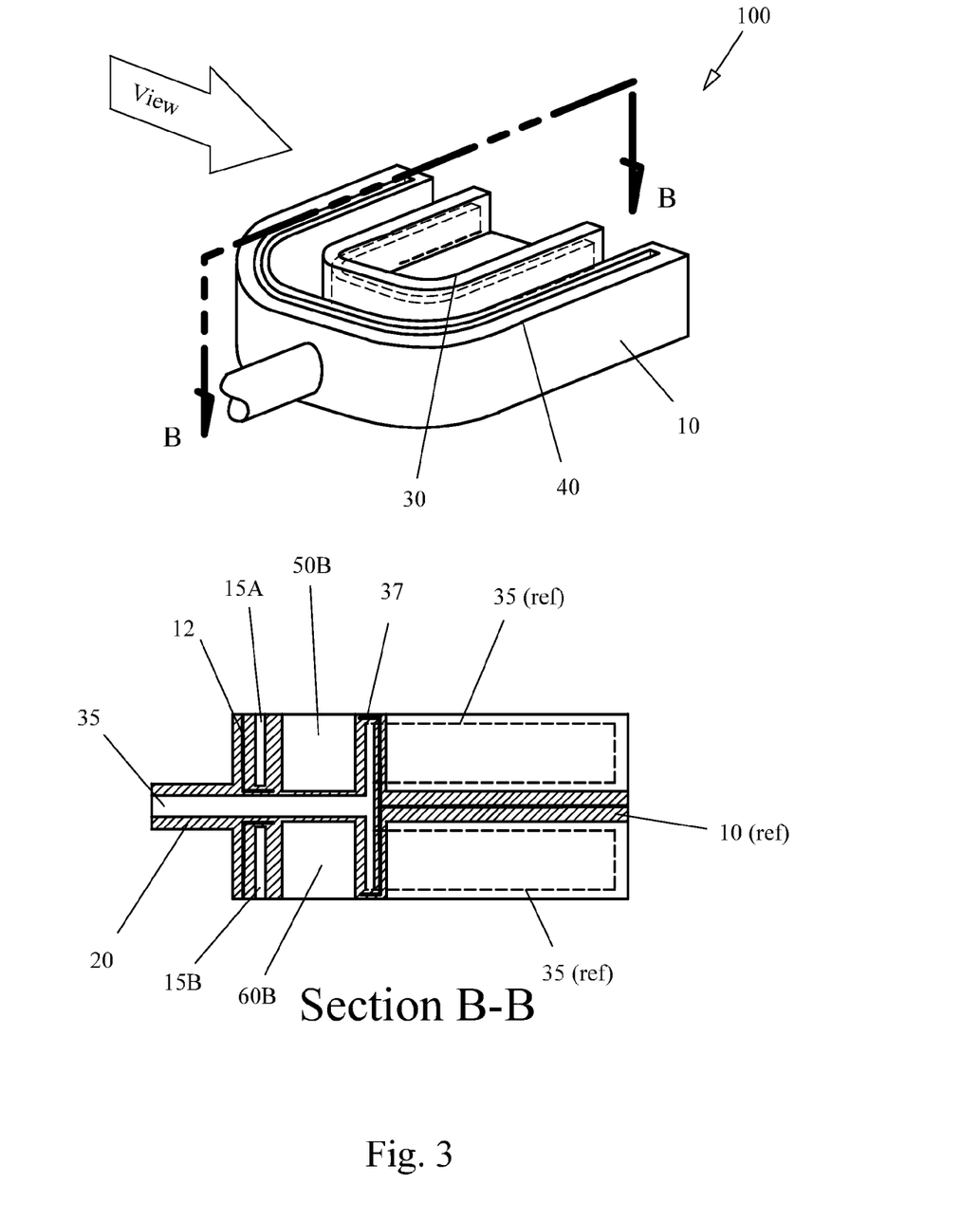
FIG. 3: is a longitudinal cross section of a first embodiment of the full mouth insert of the present invention.

Turning now to FIG. 3, the apparatus of the present invention 100 shows the full mouth insert 10 in longitudinal cross section B-B. Note that the viewing perspective is from the right side of the full mouth insert 10 towards the left. This view is taken to provide the clearest detail of the plurality of features internal to the full mouth insert 10.

Focusing tube 20 supports the waveguide means 35. Waveguide means 35 is a single unit encased in full mouth insert 10 such that x-ray energy entering the focus tube 20 is carried toward the back of the apparatus until it hits those portions of the waveguide means 35 that are contained in the inner u-shaped segment of the full mouth insert 10.

Waveguide means 35 is configured in the conventional manner, meaning that it is formed of walls with a hollow core. The walls of the waveguide means 35 are made from a material such as ceramic with an air core. While waveguide means 35 is made from ceramic, it will be recognized by those of skill in the art that other materials could be used without departing from the spirit of the invention.

The walls of the waveguide means 35 present a relatively high impedance to the x-ray energy burst, causing the majority of the x-ray energy to propagate through the air core. In this way a uniform field of x-ray energy is located around the perimeter of the inner u-shaped segment 30 capable of being projected outward through the patient's teeth toward the outer u-shaped segment containing the x-ray sensitive film.

X-ray energy from the waveguide means 35 transits the upper and lower teeth cavities 50B and 60B entering the narrow film slots 15A and 15B. X-ray energy is prevented from escaping into the patient's mouth by x-ray impeding barrier 37 and, in a similar manner, X-ray energy is prevented from escaping to the outside by x-ray impeding barrier 12. In this way the x-ray impeding barriers 12 and 37 prevent the majority of the x-ray energy from escaping the boundaries of the apparatus providing a superior level of excess radiation protection.

Figure 4:
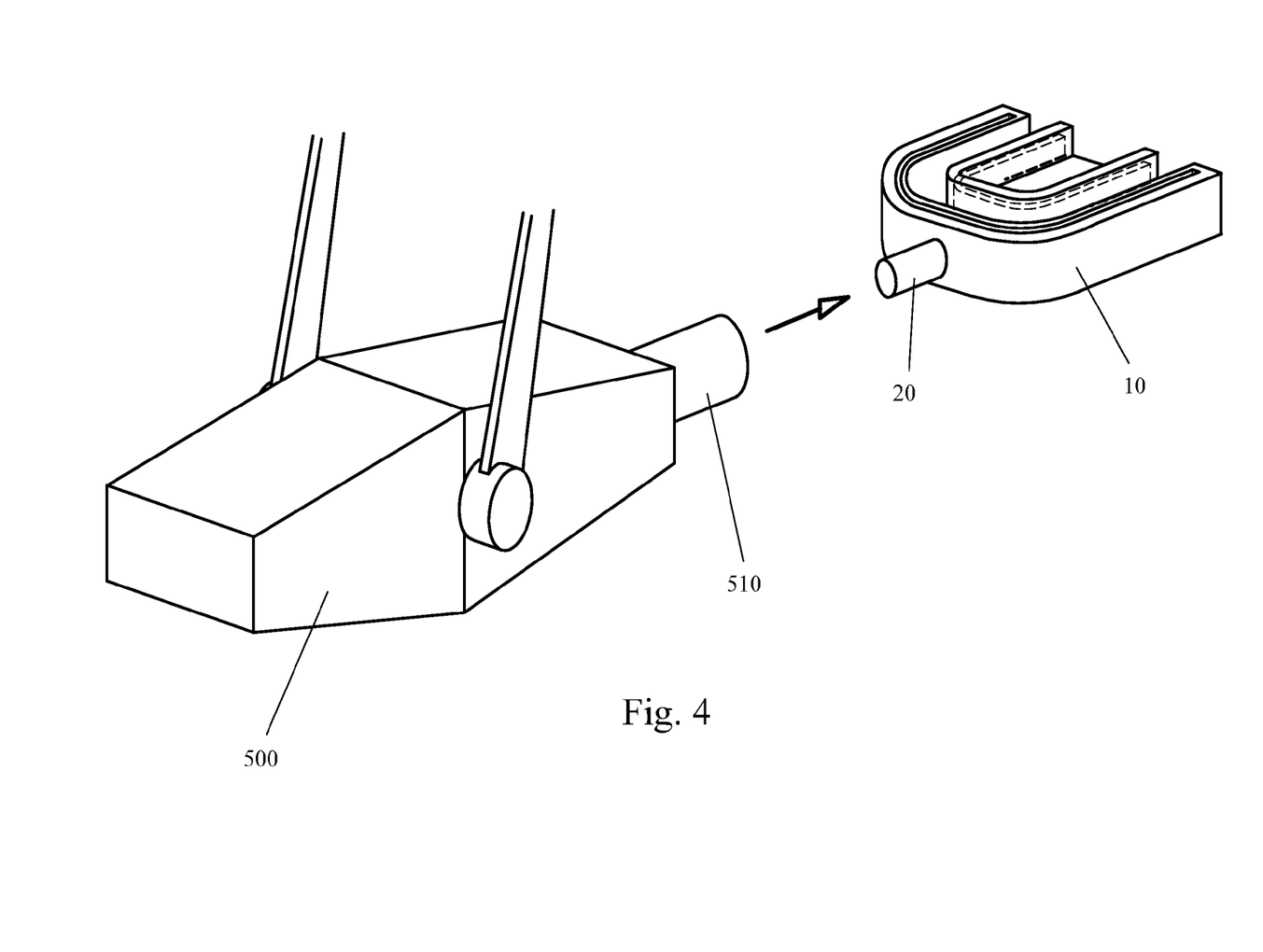
FIG. 4: shows a first embodiment of the full mouth insert of the present invention being used with a conventional x-ray transmitter.

FIG. 4 demonstrates how the first embodiment of the apparatus 10 of the present invention might be used by a conventional x-ray transmitter. Full mouth insert 10 is presumed to have been placed correctly in the mouth of a patient whose teeth are to be imaged. Conventional x-ray transmitter 500, such as the ProX series of machines from Planmeca, Inc., Roselle, Ill. mentioned above, is placed over the focusing tube 20 such that x-ray energy emitted from the transmitter 500 strikes the waveguide means [35 of FIG. 3] contained in the focus tube 20. Since the x-ray energy is propagated along the waveguide means 35 in a uniform manner, and since the film is contained, and therefore restricted, in the narrow film slots [15A and 15B of FIG. 3] of the outer u-shaped segment [40 if FIG. 2] of the full mouth insert 10, there is little possibility of misalignment, reducing the number of repeat images that must be taken and, as a result, limiting the x-radiation exposure to the patient and to the surroundings.

Figure 5:
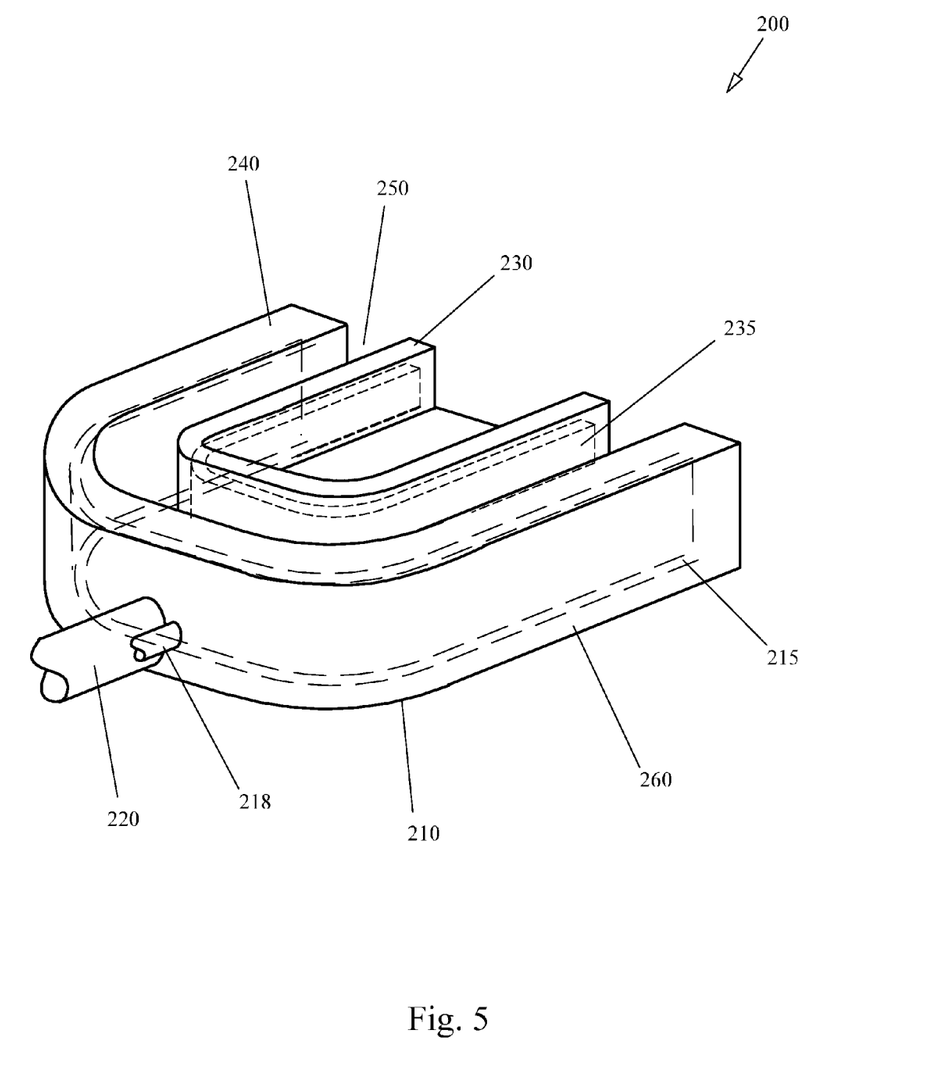
FIG. 5: shows an alternate preferred embodiment of the full mouth insert of the present invention for use with computerized imaging systems.

FIG. 5 provides an overview 200 of a second, preferred embodiment of the apparatus of the present invention. This second embodiment is for use with contemporary computer based imaging systems. A full mouth insert 210 has a pair of cavities 250 and 260 to receive the teeth of a patient to be imaged. The upper tooth cavity 250 accommodates the upper set of teeth while the lower tooth cavity 260 (not shown in detail) accommodates the lower teeth. The full mouth insert 210 can be made in several sizes to allow use on any size mouth, from early childhood to adult.

As was the case for the first embodiment, a waveguide 235 is embedded in the inner u-shaped cavity 230 and is connected to the focusing tube 220. Also as was the case for the first embodiment, the x-ray barriers in both the outer and inner u-shaped cavities 230 and 240 are present. The fact that they are not shown is for the sake of clarity, but those of skill in the art will recognize that their presence and function is as detailed above.

For this second, preferred embodiment, the film slots have been eliminated and in their place an imaging sensor 215, for example the ProSensor digital sensor from Planmeca, Inc., Roselle, Ill., has been added. This imaging sensor 215 is embedded within the outer u-shaped segment u-shaped and has a surface area that is capable of imaging a patient's entire set of teeth. The imaging sensor 215 reacts in real time to the presence of x-ray energy. The image data is transmitted via cable 218 to a computer system that analyzes and presents the image in real time for immediate review.

Figure 6:
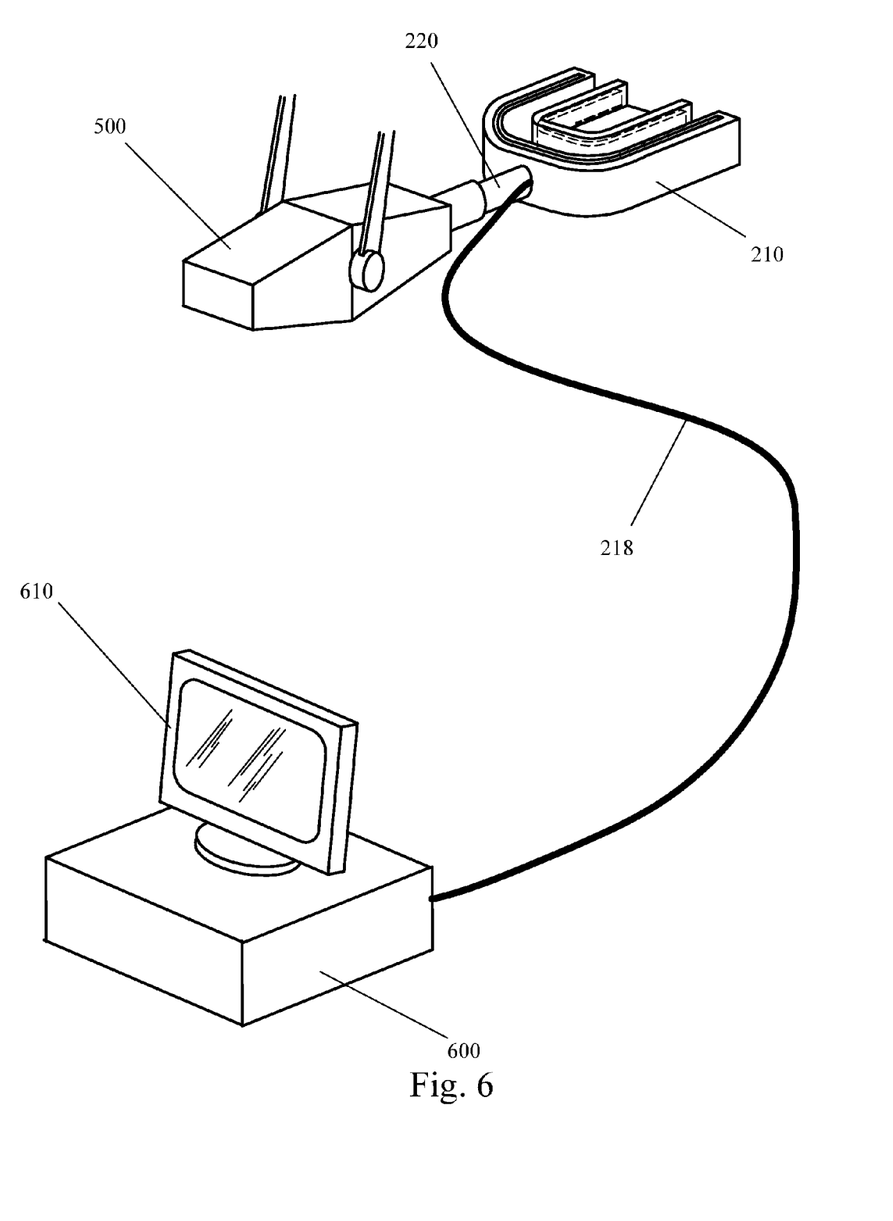
FIG. 6: shows a second, preferred embodiment of the full mouth insert of the present invention being used with a computer imaging system in concert with a conventional x-ray transmitter.

FIG. 6 demonstrates how the second preferred embodiment of the apparatus 600 of the present invention might be used by a computer imaging system. Full mouth insert 610 is presumed to have been placed correctly in the mouth of a patient whose teeth are to be imaged. Conventional x-ray transmitter 500 is placed over the focusing tube 220 such that x-ray energy emitted from the transmitter 500 strikes the waveguide means [235 of FIG. 5] contained in the focus tube 220. Since the x-ray energy is propagated along the waveguide means 235 in a uniform manner, and since the imaging sensor [215 of FIG. 5] is embedded within and therefore restricted in the outer u-shaped cavity [240 of FIG. 5] of the full mouth insert 210, there is little possibility of misalignment, reducing the number of repeat images that must be taken and, as a result, limiting the x-radiation exposure to the patient and to the surroundings. Use of this method has the additional advantage of providing images for review in real time.

Also of importance is the fact that since the various components of the apparatus of the present invention are relatively small, the full mouth insert can be made in various sizes in order to accommodate small to large jaw structures. After each use the full mouth insert can be sterilized as any other medical/dental device might be thereby improving the economics of the process.

A first advantage of the present invention is the ability to image an entire mouth with one radiation exposure. This minimizes the risk to the patient and to the technician operating the equipment.

A second advantage of the present invention is that the x-ray energy is contained. This is accomplished through the use of x-ray impeding barriers which severely attenuate radiation escape both to the inside of the patient's mouth and to the outside environment. This is a significant advantage over the prior art.

A third advantage of the present invention is that it may be used with the majority of contemporary x-ray transmitters without modification. This in turn makes the present invention very economical for the medical/dental community.

A fourth advantage of the present invention is that no misalignment possible. This occurs because the film is contained in narrow film cavities that prevent it from moving about or alternatively, an electronic imaging sensor. This feature again improves the economics of the process as well as eliminating the need for second or third exposures to get a usable image.

What is claimed is:

1. An apparatus for capturing an image of a patient's entire set of teeth in a single x-ray energy beam exposure comprised of:

a u-shaped mouthpiece, said u-shaped mouthpiece having an outer u-shaped segment and an inner u-shaped segment, said outer u-shaped segment and said inner u-shaped segment further having an upper u-shaped cavity and a lower u-shaped cavity located between said outer u-shaped segment and said inner u-shaped segment, said upper u-shaped cavity and said lower u-shaped cavity dimensioned to allow a patient's upper teeth to fit into said upper u-shaped cavity and said patient's lower teeth to fit into said lower u-shaped cavity;

a u-shaped image sensor embedded within said outer u-shaped segment, said u-shaped image sensor reactive to impinging x-ray energy and having a surface area capable of generating an image of said patient's entire set of teeth;

an outer x-ray beam energy barrier located between the outer surface of said u-shaped image sensor embedded within said outer u-shaped segment and the outer surface of said outer u-shaped segment, said outer x-ray barrier suitable for significantly attenuating impinging x-ray energy;

a focusing tube protruding from the front of said outer surface of said outer u-shaped segment, said focusing tube having at its center a waveguide means suitable for transmitting substantially unattenuated x-ray energy to the interior of said inner u-shaped segment;

an inner waveguide means located within said inner u-shaped segment, said inner waveguide means conforming to the shape of said inner u-shaped segment and interfacing with said focusing tube waveguide means such that x-ray energy entering said focusing tube waveguide means passes substantially unattenuated to said inner waveguide means;

an inner x-ray beam energy barrier located between the inner boundary of said inner waveguide means and the inner surface of said inner u-shaped segment, said inner x-ray barrier suitable for significantly attenuating impinging x-ray energy, and;

an interface cable attached at a first end to said u-shaped image sensor within said outer u-shaped segment and a second end of said interface cable capable of being attached to a computer system such that said x-ray energy impinging upon said u-shaped image sensor generates data interpretable by said computer system thereby presenting a real time image of said patient's entire set of teeth.

2. The u-shaped image sensor of claim 1 wherein said u-shaped image sensor is used with contemporary x-ray machine outputs in the range of 50-70 kVp at 5-7 mA.

3. The waveguide means of claim 1 wherein said waveguide means is tuned for input energy bursts in the range of 50-70 kVp at 5-7 mA.

4. The u-shaped mouthpiece of claim 1 wherein said u-shaped mouthpiece is formed from plastic.

5. The u-shaped mouthpiece of claim 1 wherein said u-shaped mouthpiece is formed in a range of sizes to accommodate a range of patient ages.

6. The outer and inner x-ray barriers of claim 1 wherein said inner and outer a-ray barriers are made from 0.12 mm lead foil.

7. The waveguide means of claim 1 wherein said waveguide means is made of ceramic.

8. The imaging film of claim 7 wherein said imaging film is used with contemporary x-ray machine outputs in the range of 50-70 kVp at 5-7 mA.

9. The waveguide means of claim 7 wherein said waveguide means is tuned for input energy bursts in the range of 50-70 kVp at 5-7 mA.

10. The u-shaped mouthpiece of claim 7 wherein said u-shaped mouthpiece is formed from plastic.

11. The u-shaped mouthpiece of claim 7 wherein said u-shaped mouthpiece is formed in a range of sizes to accommodate a range of patient ages.

12. The outer and inner x-ray barriers of claim 7 wherein said inner and outer a-ray barriers are made from 0.12 mm lead foil.

13. The waveguide means of claim 1 wherein said waveguide means is made of ceramic.

14. An apparatus for capturing an image of a patient's entire set of teeth in a single x-ray energy beam exposure comprised of:
   a u-shaped mouthpiece, said u-shaped mouthpiece having an outer u-shaped segment and an inner u-shaped segment, said outer u-shaped segment and said inner u-shaped segment further having an upper u-shaped cavity and a lower u-shaped cavity located between said outer u-shaped segment and said inner u-shaped segment, said upper u-shaped cavity and said lower u-shaped cavity dimensioned to allow a patient's upper teeth to fit into said upper u-shaped cavity and said patient's lower teeth to fit into said lower u-shaped cavity;
   a first narrow u-shaped segment located in the top of said outer u-shaped segment and a second narrow u-shaped segment located in the bottom of said outer u-shaped segment, both first and second of said u shaped segments conforming to the shape of said outer u-shaped segment and suitable for receiving a strip of imaging film;
   an outer x-ray beam energy barrier located between the outer boundary of said first and said second narrow u shaped segments and the outer surface of said outer u-shaped segment, said outer x-ray barrier suitable for significantly attenuating impinging x-ray energy;
   a focusing tube protruding from the front of said outer surface of said outer u-shaped segment, said focusing tube having at its center a waveguide means suitable for transmitting substantially unattenuated x-ray energy to the interior of said inner u-shaped segment;
   an inner waveguide means located within said inner u-shaped segment, said inner waveguide means conforming to the shape of said inner u-shaped segment and interfacing with said focusing tube waveguide means such that x-ray energy entering said focusing tube waveguide means passes substantially unattenuated to said inner waveguide means, and;
   an inner x-ray beam energy barrier located between the inner boundary of said inner waveguide means and the inner surface of said inner u-shaped segment, said inner x-ray barrier suitable for significantly attenuating impinging x-ray energy such that said x-ray energy impinging upon said film strips located within said first and said second narrow u shaped segments produces a film image of said patient's entire set of teeth.

\* \* \* \* \*